(12) United States Patent
Tsubata

(10) Patent No.: US 6,623,435 B2
(45) Date of Patent: Sep. 23, 2003

(54) PULSE WAVE DETECTING APPARATUS

(75) Inventor: Keisuke Tsubata, Chiba (JP)

(73) Assignee: Seiko Instruments Inc. (JP)

( * ) Notice: Subject to any disclaimer, the term of this patent is extended or adjusted under 35 U.S.C. 154(b) by 206 days.

(21) Appl. No.: 09/878,100

(22) Filed: Jun. 8, 2001

(65) Prior Publication Data

US 2002/0004636 A1 Jan. 10, 2002

(51) Int. Cl.[7] .................... A61B 5/02; A61B 5/024; A61B 5/0245
(52) U.S. Cl. .................. 600/502; 600/500
(58) Field of Search ................ 600/500–503

(56) References Cited

U.S. PATENT DOCUMENTS

| | | | | |
|---|---|---|---|---|
| 6,045,509 A | * | 4/2000 | Caro et al. ............... | 600/500 |
| 6,358,201 B1 | * | 3/2002 | Childre et al. ........... | 600/500 |
| 6,364,842 B1 | * | 4/2002 | Amano et al. ........... | 600/500 |
| 6,447,456 B1 | * | 9/2002 | Tsubata .................... | 600/503 |

FOREIGN PATENT DOCUMENTS

| | | | |
|---|---|---|---|
| JP | 05207979 | * | 8/1993 |
| JP | 07227383 | * | 8/1995 |

* cited by examiner

Primary Examiner—Joseph Pelham
(74) Attorney, Agent, or Firm—Adams & Wilks

(57) ABSTRACT

There is provided a pulse wave detecting apparatus capable of clearly discriminating pulsations from noise having a small storage amount and also a small computation amount. In the pulse wave detecting apparatus, while an oscillator unit transmits ultrasonic waves toward an object under examination and a receiver receives reflection waves reflected from the object under examination, a detecting unit converts the reflection waves from the pulse waves. A pulsation detecting unit predicts timing of a next pulsation from an interval of previously acquired pulsation and pulse, detects a peak of a pulse wave which is larger than a predetermined value within the zone Z located before/after the predicted timing of the pulsation. Then, this pulsation detecting unit specifies such a peak having a timing which is located at the nearest timing with respect to the predicted timing among each of these peaks.

7 Claims, 9 Drawing Sheets

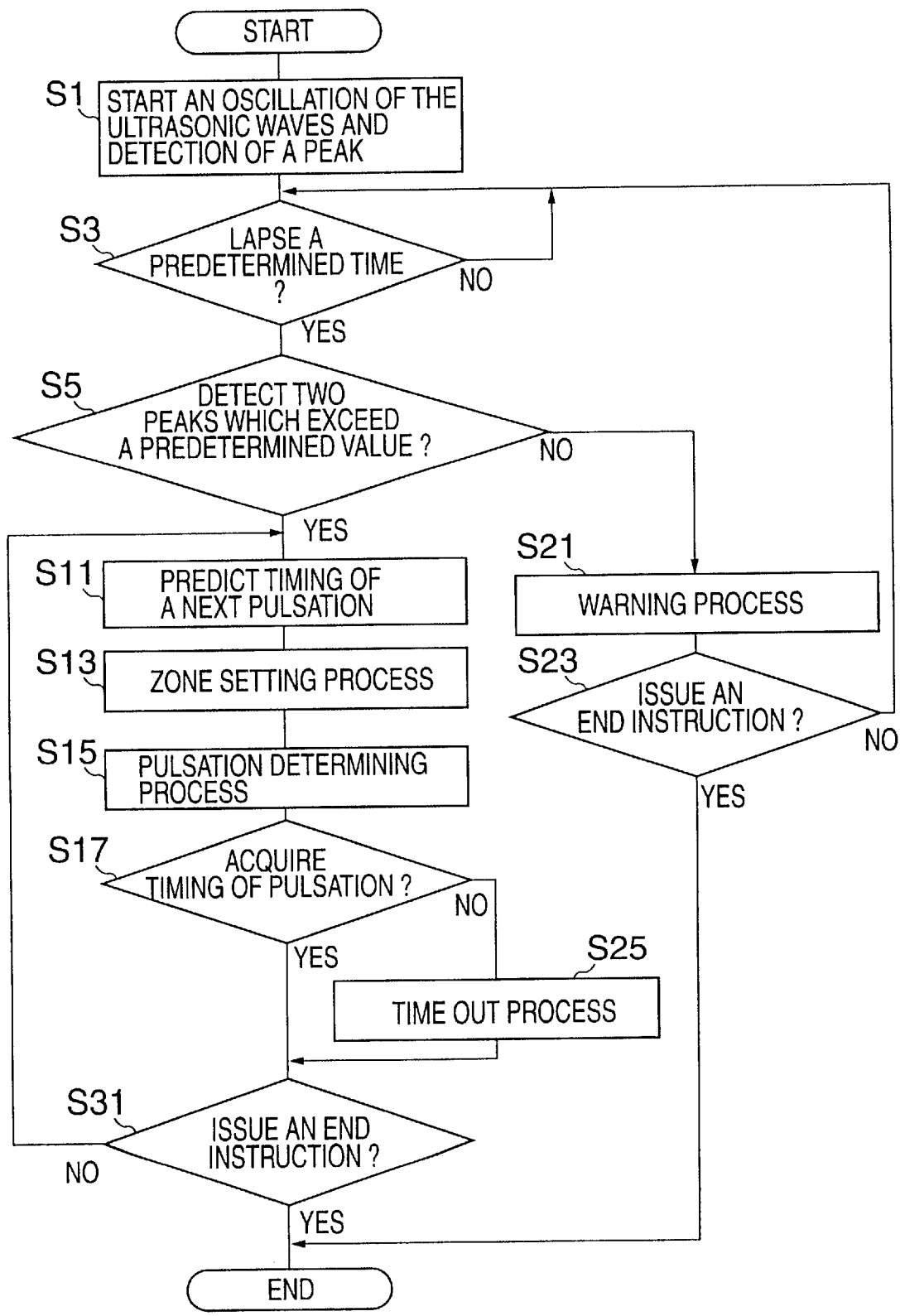

FIG. 5

| | INTERVALS "RR" | PULSE RATES | CHANGING RATIO OF THE INTERVALS "RR" | | INTERVALS "RR" | PULSE RATES | CHANGING RATIO OF THE INTERVALS "RR" |
|---|---|---|---|---|---|---|---|
| 1 | 912 | 65.8 | | 51 | 888 | 67.6 | 90.1 |
| 2 | 934 | 64.2 | 102.4 | 52 | 858 | 69.9 | 96.6 |
| 3 | 954 | 62.9 | 102.1 | 53 | 850 | 70.6 | 99.1 |
| 4 | 920 | 65.2 | 96.4 | 54 | 846 | 70.9 | 99.5 |
| 5 | 920 | 65.2 | 100.0 | 55 | 902 | 66.5 | 106.6 |
| 6 | 940 | 63.8 | 102.2 | 56 | 952 | 63.0 | 105.5 |
| 7 | 952 | 63.0 | 101.3 | 57 | 928 | 64.7 | 97.5 |
| 8 | 948 | 63.3 | 99.6 | 58 | 948 | 63.3 | 102.2 |
| 9 | 986 | 60.9 | 104.0 | 59 | 986 | 60.9 | 104.0 |
| 10 | 986 | 60.9 | 100.0 | 60 | 950 | 63.2 | 96.3 |
| 11 | 972 | 61.7 | 98.6 | 61 | 972 | 61.7 | 102.3 |
| 12 | 992 | 60.5 | 102.1 | 62 | 988 | 60.7 | 101.6 |
| 13 | 988 | 60.7 | 99.6 | 63 | 958 | 62.6 | 97.0 |
| 14 | 946 | 63.4 | 95.7 | 64 | 984 | 61.0 | 102.7 |
| 15 | 982 | 61.1 | 103.8 | 65 | 1000 | 60.0 | 101.6 |
| 16 | 978 | 61.3 | 99.6 | 66 | 982 | 61.1 | 98.2 |
| 17 | 944 | 63.6 | 96.5 | 67 | 996 | 60.2 | 101.4 |
| 18 | 1002 | 59.9 | 106.1 | 68 | 1012 | 59.3 | 101.6 |
| 19 | 1010 | 59.4 | 100.8 | 69 | 986 | 60.9 | 97.4 |
| 20 | 962 | 62.4 | 95.2 | 70 | 1012 | 59.3 | 102.6 |
| 21 | 1006 | 59.6 | 104.6 | 71 | 1018 | 58.9 | 100.6 |
| 22 | 992 | 60.5 | 98.6 | 72 | 994 | 60.4 | 97.6 |
| 23 | 966 | 62.1 | 97.4 | 73 | 1024 | 58.6 | 103.0 |
| 24 | 986 | 60.9 | 102.1 | 74 | 990 | 60.6 | 96.7 |
| 25 | 960 | 62.5 | 97.4 | 75 | 954 | 62.9 | 96.4 |
| 26 | 952 | 63.0 | 99.2 | 76 | 982 | 61.1 | 102.9 |
| 27 | 1014 | 59.2 | 106.5 | 77 | 998 | 60.1 | 101.6 |
| 28 | 1002 | 59.9 | 98.8 | 78 | 988 | 60.7 | 99.0 |
| 29 | 1032 | 58.1 | 103.0 | 79 | 1034 | 58.0 | 104.7 |
| 30 | 1070 | 56.1 | 103.7 | 80 | 1046 | 57.4 | 101.2 |
| 31 | 1036 | 57.9 | 96.8 | 81 | 1026 | 58.5 | 98.1 |
| 32 | 1054 | 56.9 | 101.7 | 82 | 1064 | 56.4 | 103.7 |
| 33 | 1062 | 56.5 | 100.8 | 83 | 1036 | 57.9 | 97.4 |
| 34 | 1002 | 59.9 | 94.4 | 84 | 988 | 60.7 | 95.4 |
| 35 | 1030 | 58.3 | 102.8 | 85 | 1008 | 59.5 | 102.0 |
| 36 | 1018 | 58.9 | 98.8 | 86 | 1016 | 59.1 | 100.8 |
| 37 | 956 | 62.8 | 93.9 | 87 | 982 | 61.1 | 96.7 |
| 38 | 1010 | 59.4 | 105.6 | 88 | 1000 | 60.0 | 101.8 |
| 39 | 1024 | 58.6 | 101.4 | 89 | 992 | 60.5 | 99.2 |
| 40 | 992 | 60.5 | 96.9 | 90 | 944 | 63.6 | 95.2 |
| 41 | 1042 | 57.6 | 105.0 | 91 | 982 | 61.1 | 104.0 |
| 42 | 1042 | 57.6 | 100.0 | 92 | 980 | 61.2 | 99.8 |
| 43 | 1006 | 59.6 | 96.5 | 93 | 938 | 64.0 | 95.7 |
| 44 | 1048 | 57.3 | 104.2 | 94 | 970 | 61.9 | 103.4 |
| 45 | 1020 | 58.8 | 97.3 | 95 | 974 | 61.6 | 100.4 |
| 46 | 962 | 62.4 | 94.3 | 96 | 934 | 64.2 | 95.9 |
| 47 | 976 | 61.5 | 101.5 | 97 | 952 | 63.0 | 101.9 |
| 48 | 982 | 61.1 | 100.6 | 98 | 956 | 62.8 | 100.4 |
| 49 | 970 | 61.9 | 98.8 | 99 | 962 | 62.4 | 100.6 |
| 50 | 986 | 60.9 | 101.6 | 100 | 972 | 61.7 | 101.0 |

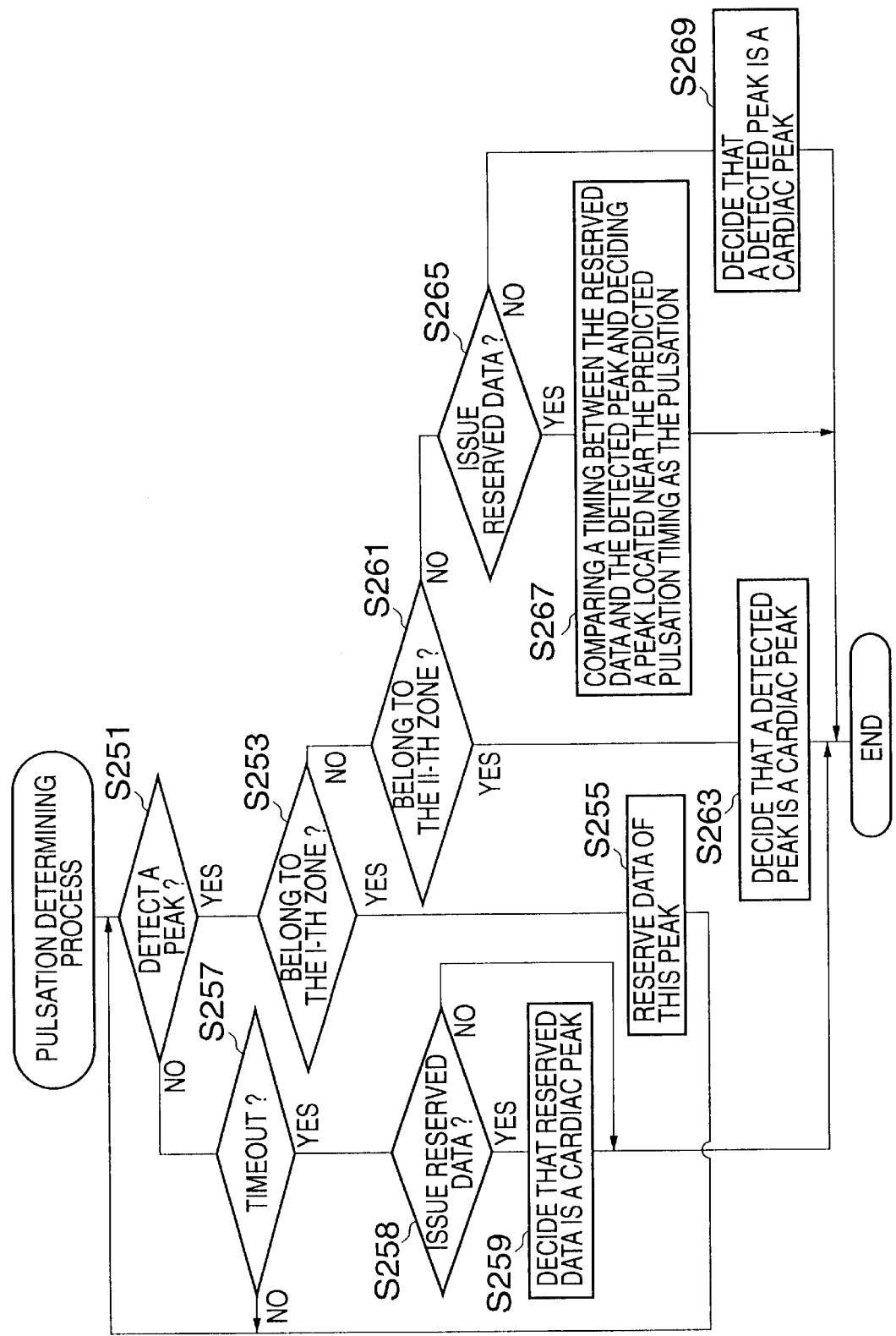

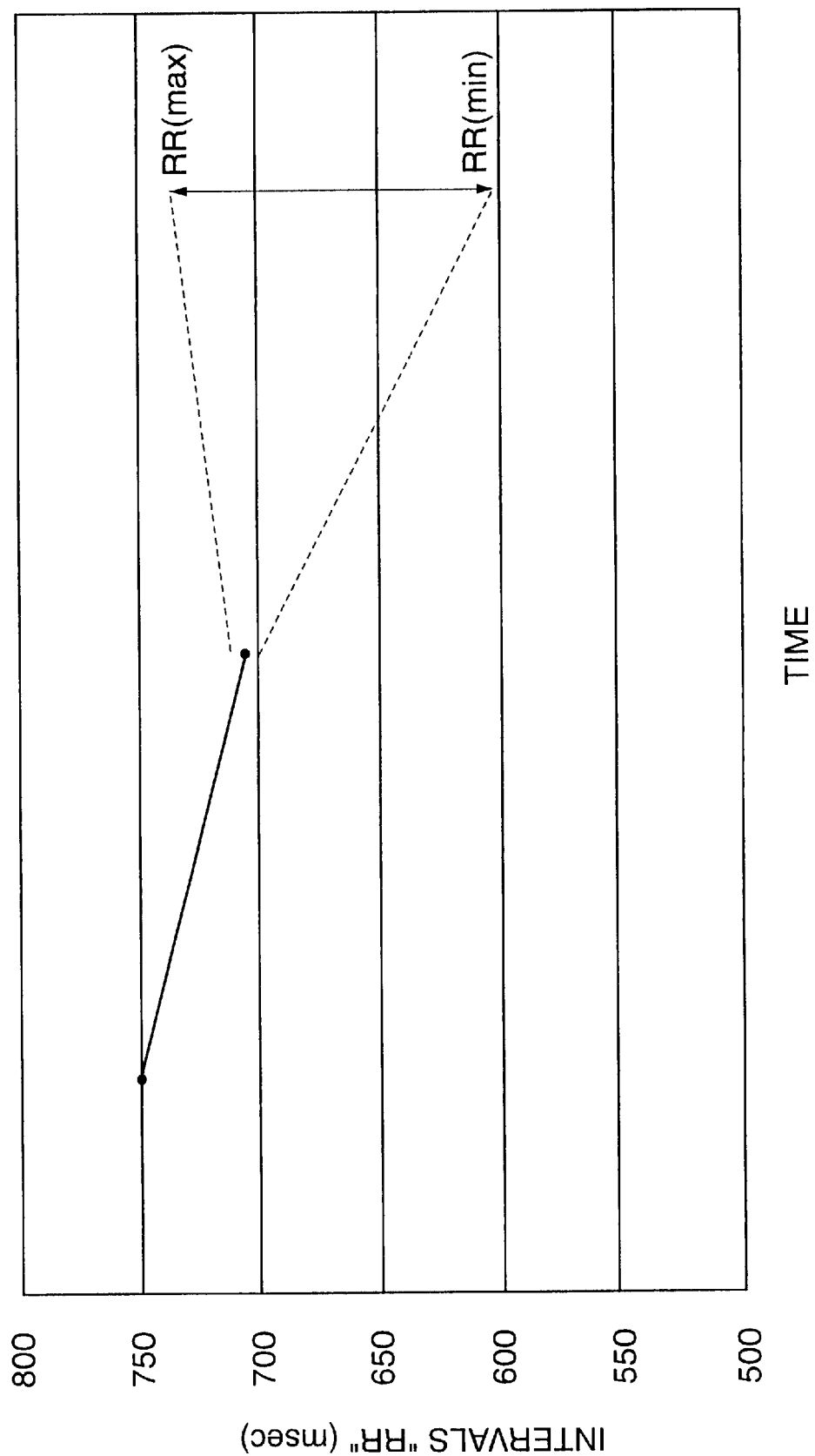

PULSE WAVE DETECTING APPARATUS

BACKGROUND OF THE INVENTION

1. Field of the Invention

The present invention generally relates to a pulse wave detecting apparatus. More specifically, the present invention is directed to a pulse wave detecting apparatus capable of clearly discriminating pulsations from noise, while having a small storage amount and also a small computation amount.

2. Description of the Related Art

In medical fields and also when performing health care administrations, detections of pulse waves by measuring blood f lows within arteries are widely carried out. To detect such pulse waves, palpation is carried out. In addition, using pulse wave detecting apparatus, the pulse rate is automatically and electronically detected to detect such pulse waves.

As an apparatus capable of electronically detecting pulse waves to obtain pulse rates, there are various types of apparatuses, for instance, one pulse wave detecting apparatus operated in such a manner that while a piezoelectric-effect type element is positioned as a sensor over an artery, a pulse rate is detected based upon a change contained in pressure of a skin surf ace (namely, displacement of skin surface caused by pressure) in connection with a pressure change occurred within this artery, and another detecting apparatus capable of detecting a pulsatory number is operated by using ultrasonic waves.

Then, in such pulse wave detecting apparatus, pulse wave signals need to be discriminated from noise.

As the conventional technique for discriminating the pulse wave signals from the noise, there is known for instance, Japanese Laid-open Patent Application Laid-open No. Hei-7-227383 describes the method of using the frequency analysis. In this conventional discrimination method, while the data containing the noise are stored for a predetermined time period, the frequency analysis such as FFT (Fast Fourier Transform) is carried out with respect to the stored data so as to calculate the average pulse within a preselected time period.

However, in such a conventional pulse wave detecting apparatus capable of discriminating the pulse wave signals from the noise by utilizing the frequency analysis, vary large amounts of data are required to be stored in order to execute the frequency analysis. Only the averaged pulse rate within a preselected time section requiring a storage unit having a large storage capacity, and requiring a lengthy calculation time since the calculation amount is large is detected. Only noise produced in the regular mode which cannot acquire a change in the respective pulse waves and fluctuations of pulsations and the like is recognized as noise. However, noise which is produced in the irregular mode cannot be discriminated from the pulse wave signal. Under such a circumstance, higher discriminative improvements are required in the conventional pulse wave detecting apparatus.

SUMMARY OF THE INVENTION

The present invention has been made to solve the above-described problems of the conventional pulse wave detecting apparatus, and therefore, has an object to provide such a pulse wave detecting apparatus clearly capable of discriminating pulsation from noise, while requiring a small storage capacity of acquired data and also a small calculation amount in a calculation of a pulse wave detection.

To achieve the above-explained object, a pulse wave detecting apparatus (first arrangement) is provided, according to an aspect of the present invention, featured by comprising: pulse wave detecting means for detecting a pulse wave; pulsation predicting means for predicting timing of a pulsation based upon the pulse wave detected by the pulse wave detecting means; range determining means for determining predetermining widths located before/after the timing of the pulsation predicted by the pulsation predicting means; pulsation subject extracting means for extracting a subject for pulsation from the pulse wave detected by the pulse wave detecting means in the predetermined widths determined by the range determining means; and pulsation specifying means for specifying a pulse among the subjects extracted by the pulsation subject extracting means.

In the pulse wave detecting apparatus of the present invention, since the pulsation is detected from the pulse waves located in the predetermined widths before/after the predicted timing of the pulsation, the data used to detect the pulsation can be reduced. Also, while such a storage unit having a large storage capacity used to detect the pulsation is not required, a calculation amount required to detect the pulsation is also reduced.

Also, in the pulse wave detecting apparatus having the first arrangement, such a pulse wave detecting apparatus having a second arrangement according to the present invention is provided in which the pulsation predicting means predicts the timing of the next pulsation movement based upon an interval of a previously acquired pulsation, or a pulse rate.

In the pulse wave detecting apparatus having either the first arrangement or the second arrangement, such a pulse wave detecting apparatus having a third arrangement according to the present invention is provided in which the pulsation specifying means determines a pulse based upon both the timing predicted by the pulsation predicting means and the timing of the pulsation subject extracted by the pulsation subject extracting means.

Further, in the pulse wave detecting apparatus having the third arrangement, a pulse wave detecting apparatus having a fourth arrangement according to the present invention is provided in which the range determining means subdivides the predetermined widths located before/after the predicted timing of the pulsation into a plurality of zones containing both a first zone located earlier than the predicted timing of the pulsation and a second zone subsequent to the first zone which contains the predicted timing of the pulsation, and determines the predetermined widths; and the pulsation specifying means immediately specifies a pulsation subject which is first detected in the second zone as the pulsation.

Further, a pulse wave detecting apparatus is provided, a pulse wave detector to detect a pulse wave; a pulsation predicting circuit to predict timing of a pulsation based upon the pulse wave detected by the pulse wave detector; a range determining circuit to determine predetermining widths located before/after the timing of the pulsation predicted by the pulsation predicting circuit; a pulsation subject extracting circuit to extract a subject for pulsation from the pulse wave detected by the pulse wave detector in said predetermined widths determined by the range determining circuit; and a pulsation specifying circuit to specify a pulse from among the subjects extracted by the pulsation subject extracting circuit.

BRIEF DESCRIPTION OF THE DRAWINGS

For a better understanding of the present invention, reference is made of a detailed description in conjunction with the accompanying drawings, in which:

FIG. 2 is a flow chart for describing a process flow operation of a pulse wave detecting process executed by the pulse wave detecting apparatus of FIG. 1;

FIG. 5 is a table representative of results in such a manner that while pulse signals "P" are detected during rest/relax states, a calculation is made of pulse rates "N", intervals "RR" between present pulse signals "P" and preceding pulse signals "P", and also a ratio of changes in the intervals "RR" of pulsations;

FIG. 6 are graphical representations made from the table of FIG. 5.

FIG. 10 is a flow chart for explaining a flow operation of a pulsation determining process executed by the pulse wave detecting apparatus of the third embodiment; and FIG. 11 is an explanatory diagram for describing a method for determining predetermined time "t" in another embodiment of the present invention.

DETAILED DESCRIPTION OF THE PREFERRED EMBODIMENTS

Referring now to FIGS. 1 to 10, a detailed description will be made of pulse wave detecting apparatus according to preferred embodiments of the present invention.

(1). Summary of the Present Embodiment

In a pulse wave detecting apparatus of the present embodiment, ultrasonic waves "f0" having a frequency of 10 MHz emitted from an oscillator 11 are transmitted from a body surface toward an artery 2 (oscillation means), and reflection waves "f1" are received by a receiver 21 (reception means). The reflection waves "f1" are frequency-modulated by the Doppler effect of blood flows corresponding to a reflection object (namely, object under measurement). Then, since this reception wave is FM-detected, a desirable pulse wave is extracted. A pulsation is detected as a peak of this extracted pulse wave.

In this embodiment, based upon an interval between a pulsation "P00" and another pulsation "P0" which have already been detected, and further based on a timing of this pulsation "P0", timing of a pulsation "P1" subsequent to "P0" is predicted. Also, such a peak detected within a predetermined range defined before/after the predicted timing of the pulsation "P1" is specified as the pulsation "P1".

As previously described, in this embodiment, while such a peak which is not included in the predetermined range is handled as noise based upon the previously acquired data, the pulsation may be determined only from such a peak which is contained in the predetermined range. As a result, both a storage capacity of a storage unit and a total calculation amount may be reduced, while the pulsation is discriminated from the noise.

(2). Detailed Contents of Present Embodiment

Figure 1:
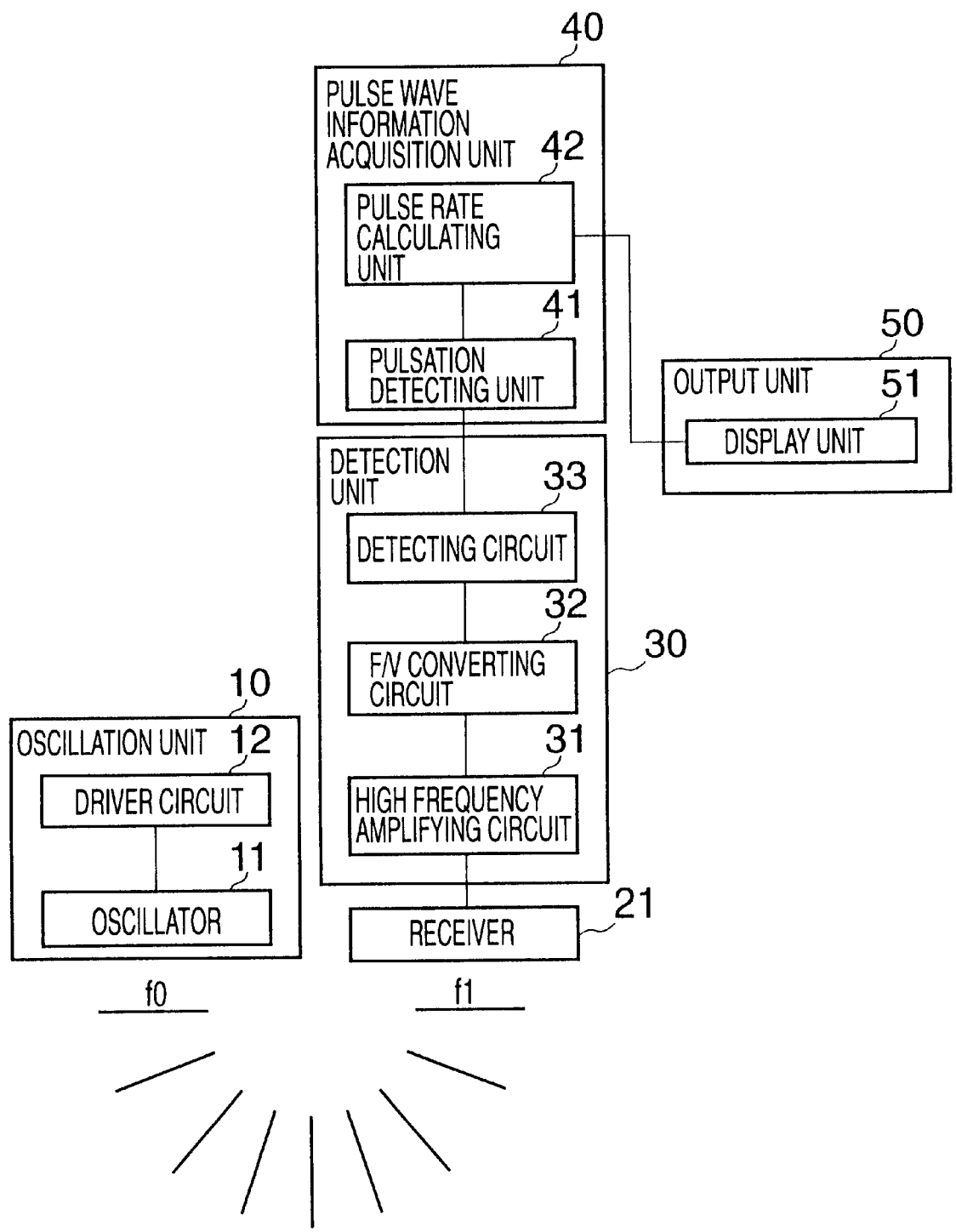
FIG. 1 is a schematic block diagram for representing an arrangement of a pulse wave detecting apparatus according to a first embodiment of the present invention.

FIG. 1 schematically indicates an arrangement of a pulse wave detecting apparatus according to a first embodiment of the present invention.

As indicated in this drawing, the pulse wave detecting apparatus is provided with an oscillation unit 10, a receiver 21, a detection unit 30, a pulse wave information acquisition unit 40, and an output unit 50. Also, this pulse wave detecting apparatus is equipped with a control unit (not shown) which contains a timer and controls the above-described units, and a storage unit (not shown).

The oscillation unit 10, the receiver 21, and the detection unit 30 may function as a pulse wave detecting means for transmitting (projecting) ultrasonic waves to an artery, and detecting pulse waves from reflection waves. The pulse wave information acquisition unit 40 may function as a pulsation predicting means, a range determining means, a pulsation subject extracting means, and also a pulsation specifying means. The pulsation predicting means enters thereinto the pulse wave detected by the detection unit 30, and predicts the timing of a pulsation based upon this pulse wave. The range determining means determines a predetermined width (zone Z) defined before/after the timing of the pulsation predicted by the pulsation predicting means. The pulsation subject extracting means detects a peak equal to a subject of a pulsation from the pulse wave which is detected in the determined predetermined width (zone Z). The pulsation specifying means specifies a pulse from the extracted subjects.

The oscillation unit 10 is equipped with an oscillator 10 arranged on a body surface of an object under examination, and a driver circuit 12 for driving the oscillator 11 so as to produce ultrasonic waves. The oscillator 11 is arranged on an artery to transmit the ultrasonic waves toward the artery.

The receiver 21 is arranged over an artery of a body surface located in the vicinity of the oscillator 11. The receiver 21 receives such ultrasonic waves which are transmitted from the oscillator 11 and are then propagated through an interior of a body containing this artery, and then supplies the received signals to the detection unit 30.

The detection unit 30 is provided with a high frequency amplifying circuit 31, an F/V converting circuit 32, and a detecting circuit 33.

The high frequency amplifying circuit 31 is a circuit which amplifies the reflecting wave f1 and supplies it to the F/V converting circuit 32.

The F/V converting circuit 32 is a circuit for outputting a voltage in response to a value of a frequency by utilizing a change contained in voltage gains in response to the frequency value.

The detecting circuit 33 is a circuit for outputting a voltage (namely, voltage waveform which is changed in response to pulse waveform) which corresponds to an envelope line thereof by detecting an amplitude.

The pulse wave information acquiring unit 40 is equipped with a pulsation detecting unit 41 and a pulse rate calculating unit 42.

The pulsation detecting unit 41 outputs the voltage waveform supplied from the detecting circuit 33 to the output unit 50, and also detects a pulsation from this voltage waveform, and then supplies the detected pulsation and timing thereof to the pulse rate calculating unit 42.

In the pulse rate calculating unit 42, a pulse rate "N" per 1 minute is calculated based upon the pulsation and the timing thereof supplied from the cardiac beat detecting unit 41. The pulse rate "N" calculated by the pulse rate calculating unit 42 is supplied to the output unit 50. The pulse rate calculating unit 42 also supplies the pulse waveform (voltage waveform) to the output unit 50.

The output unit 50 is provided with a display unit 51, and digitally displays both the pulse waveform and the pulse rate N, which are supplied from the pulse rate calculating unit 42. While the display unit 51 is constituted by a liquid crystal display unit, this display unit 51 may display the pulse rate by way of an image. Alternatively, the pulse rate may be electrically displayed on a panel.

Embodiment 1

Next, operations of the pulse wave detecting apparatus according to the first embodiment will be described.

FIG. 2 is a flow chart for describing a process flow of a pulse wave detecting process according to the first embodiment.

When the pulse wave detecting process is commenced in the first embodiment, as shown in FIG. 2, the control unit turns ON the drive signal supplied to the drive circuit 41 so as to start the oscillation of the ultrasonic waves by the oscillator 11, and controls the pulsation detecting unit 41 to detect a peak of pulse waveforms acquired from the reflection waves (step S1).

FIG. 3 represents output waveforms appeared in the respective constructive units employed in the pulse wave detecting apparatus.

Figure 3A:
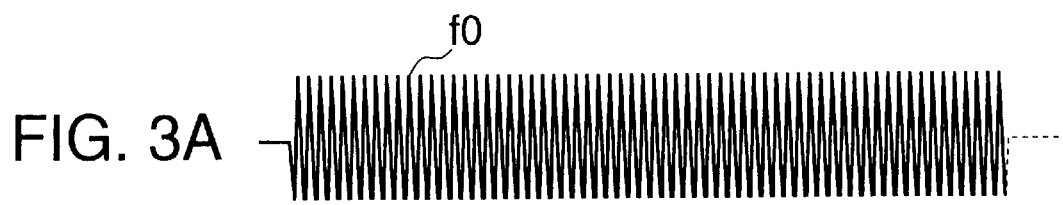
FIG. 3 are explanatory diagrams for explaining output waveforms appeared in the respective constructive units of the pulse wave detecting apparatus of FIG. 1.
Figure 3B:
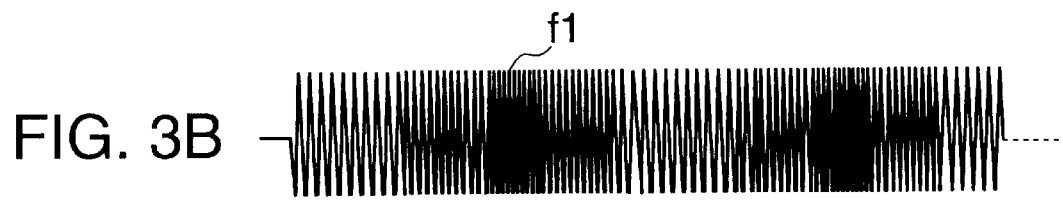
Figure 3C:
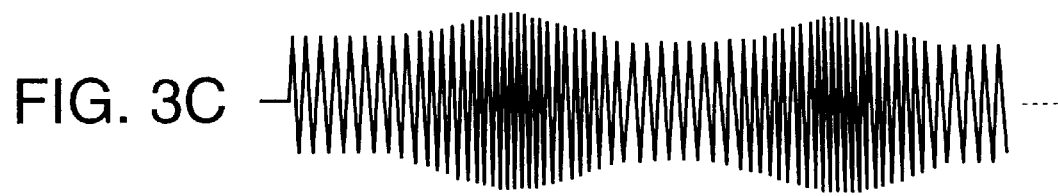

When the pulse wave detecting process is commenced, as indicated in FIG. 3A, ultrasonic waves "f0" having a preselected frequency are projected from the oscillator 11 toward an artery 2. The ultrasonic waves "f0" are reflected on blood flowing through the artery 2, and then, as indicated in FIG. 3B, reflection waves "f1" are received by the receiver 21. These reflection waves "f1" are frequency-modulated (FM-modulation) due to the Doppler effect occurred while the ultrasonic waves "f0" are reflected. A signal which is produced based on the reflection waves "f1" from the receiver 21 is amplified by the high frequency amplifying circuit 31. Thereafter, this amplified signal is converted by the F/V converting circuit 32 in such a manner that, as indicated in FIG. 3C, a frequency change of this amplified signal is converted into a change contained in voltages, namely an amplitude change. Then, in the detection circuit 33, the amplitude change is amplitude-detected, and as shown in FIG. 3D, this amplitude-detected signal is a pulse waveform whose voltage is varied in correspondence with an envelope line.

This pulse waveform is supplied to the pulsation detecting unit 41. Also, this pulse waveform is further supplied via the pulse rate calculating unit 42 to the display unit 51 so as to display thereon an image.

Figure 3D:
Figure 3E:
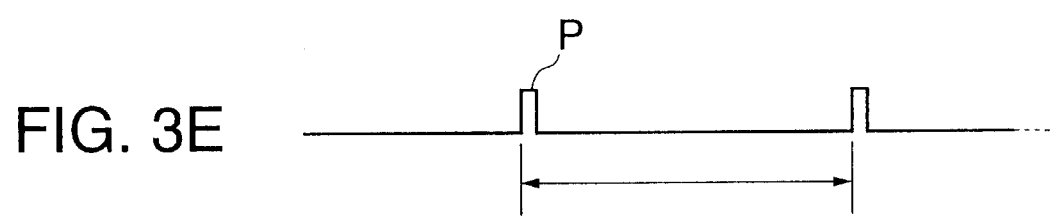

Then, in the pulsation detecting unit 41, as indicated in FIG. 3E, peaks "P" are detected from the supplied pulse waveform shown in FIG. 3D, and such a peak which exceeds a predetermined threshold among the detected peaks "P" is specified as a desirable peak corresponding to the pulsation.

When the peak "P" corresponding to the pulsation is specified, the timing at which this peak "P" is detected is stored into the storage unit. Alternatively, while voltage waveforms outputted from the detection circuit 33 are differentiated, such a peak which exceeds a preselected threshold among peaks of the differentiated waveforms may be handled as a peak corresponding to the pulsation.

Also, while the control unit detects a time lapse after the pulse wave detecting process operation is commenced (step S3), in such a case that even when a predetermined time period has passed (YES at step S3), two peaks which exceed a predetermined value are not detected (NO at step S5), the control unit causes the display unit 41 to display as a warning process the possibility that the sensor is displaced, or produces beep sounds in order to give attention to a person applied with the sensor (step S21).

At the same time as when the warning process is carried out, an end instructing button is displayed, and an inquiry indication that such as to stop measurement is displayed, so that the end instruction may be entered. When the end instruction is issued (YES at step S23), the pulse wave detecting process is immediately ended. To the contrary, when the end instruction is not issued (NO at step S23), the timer is reset to "0", and the process is returned to the previous step S3. At this step S3, the detection process of another peak is again carried out for a preselected time period after the process returning time instant.

In the case that two sets of peaks which are larger than, or equal to the determined value within a predetermined time period (YES at step S3 and YES at step S5), timing at which these two peaks are detected is outputted from the storage unit to the pulse rate calculating unit 42 in order to calculate a pulse rate "N". The calculated pulse rate "N" is outputted to the display unit 51 so as to be displayed thereon.

After the two peaks larger than, or equal to the predetermined threshold have been detected, pulse waveforms also are continuously entered into the pulsation detecting unit 41. The control unit causes this pulsation detecting unit 41 to predict timing of a next pulsation from the timing of the two detected peaks (step S11), and sets such a zone based upon this timing prediction (step S13). In this zone, there are great possibilities that a peak which is detected subsequent to these two detected peaks is caused by a pulsation.

Figure 4:
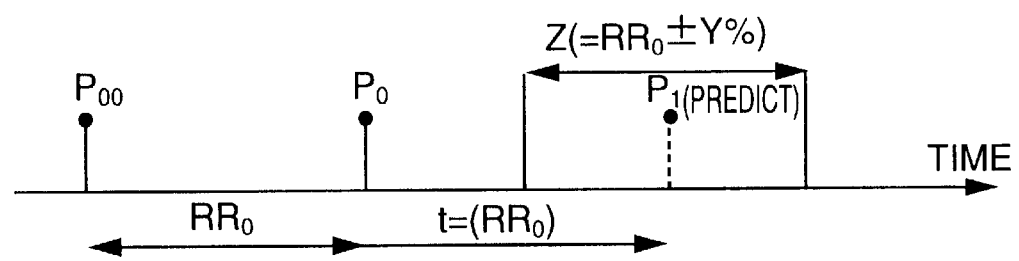
FIG. 4 is an explanatory diagram for explaining predictions of subsequent pulsation timing by a pulsation detecting unit, and also setting operation of zones in the pulse wave detecting apparatus of FIG. 1.

FIG. 4 is an explanatory diagram for explaining that timing of the next pulsation is predicted by the pulsation detecting unit 41 and the zone is set.

As indicated in FIG. 4, in accordance with this first embodiment, timing of a subsequent pulsation "P1" is predicted, assuming that a time interval "RR0" is equal to a time interval "t". This time interval "RR0" is defined between the latest (final) peak "P0" which is specified as the pulsation and another peak "P00" appeared before this latest peak "P0". This time interval "t" is defined from the latest peak "P0" specified as the pulsation up to the next pulsation "P1". In other words, such timing after the timing of the pulsation "P0" by "t (=RR0)" is predicted as the timing of the next pulsation.

As previously described, in accordance with this first embodiment, in order to predict the next pulsation, the pulse interval "RR" defined between the two pulsations which have been acquired before this next pulsation is predicted is utilized. As a result, while a total calculation amount required to predict the next pulsation can be reduced, the storage capacity required to predict the next pulsation can be suppressed to a small storage capacity.

In a zone setting process defined at a step S13, a zone "Z" is set to Y% of the pulsation interval RR0(=t) before and after such timing of the next predictable pulsation.

In other words, the zone "Z" is defined as follows: that is, a time instant of t×100−Y)/100 after a peak "P0" of a pulsation just before the predictable next pulsation constitutes a starting point, whereas another time instant of t×(100+Y)/100 after the above-explained peak "P0" constitutes an ending point.

Figure 6A:
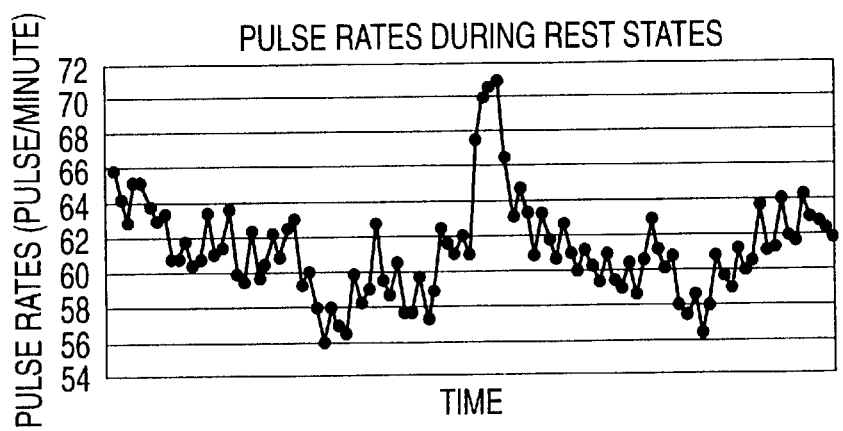
FIG. 6A is a graph for indicating a time-lapse change in the pulse rates "N"
Figure 6B:
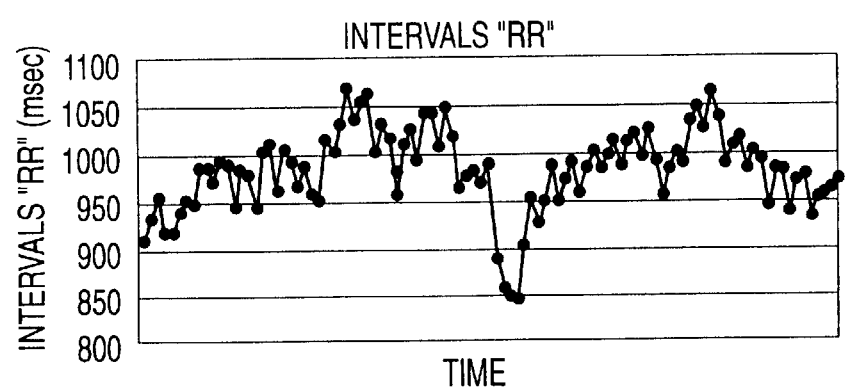
FIG. 6B is a graph for showing a time-lapse change in the intervals "RR" of the pulsations.
Figure 6C:
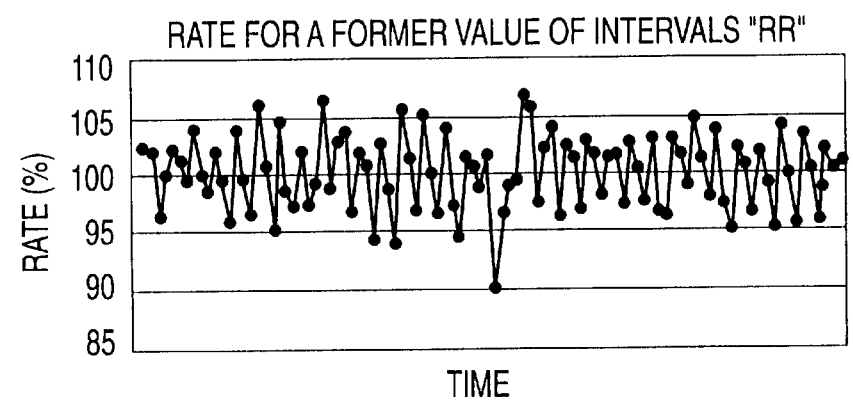
FIG. 6C is a graph for indicating a changing ratio of the intervals "RR" of the pulsations.

FIG. 5 is a table representing results in such a manner that while pulsations "P" are detected during rest/relax states, a calculation is made of pulse rates "N", intervals "RR" between present pulsations "P" and preceding pulsations "P", and also a ratio of changes in the intervals "RR" of pulsations. FIG. 6 are graphical representations made from the table of FIG. 5, i.e., FIG. 6A is a graph for indicating a time-lapse change in the pulse rates "N", FIG. 6B is a graph for showing a time-lapse change in the intervals "RR" of the pulsations, and FIG. 6C is a graph for indicating a changing ratio of the intervals "RR" of the pulsations.

As indicated in FIGS. 5 and 6, during the rest/relax states, both the interval "PR" of the present pulsations and the pulse rate "N" are located within a range of approximately ±10% with respect to both the interval "RR" of the preceding pulsation and the pulse rate "N". In other words, with respect to timing after a time interval equal to the time interval "RR" of the preceding pulsation (namely, predictable timing of the next pulsation), the next pulsation "P" is actually detected for a time duration between the preceding 10% of the pulsation interval "RR" and the succeeding 10% thereof.

As a consequence, while the pulse waves are detected during the rest/relax states, the zone "Z" is set to 10% of a predetermined time "t", respectively, so that most of these pulse waves may be detected. Further, when the zone "Z" is set to 20% of this predetermined time "t", these pulse waves can be substantially completely detected. In addition, if the zone "Z" is set to more than 20% of this predetermined time "t", then the pulse wave detection precision can be furthermore improved. However, when a ratio of this zone with respect to the predetermined time "t" is increased, since the power consumption is increased, this zone "Z" may be preferably set to time ranges between approximately 20% and 50% of the predetermined time "t". Although not in the drawing, since the fluctuations of the pulse waves during motion states and tension states are decreased, as compared with those during rest/relax states, even if the zone "Z" is set to less than 20%, for instance, 10% to 15% of the predetermined time "t", then the pulse waves may be substantially correctly detected.

It should be noted that the length of the zone "Z" (value of Y) may be determined as follows. That is, this zone length may be determined by judging as to whether the subject under examination is in a rest/relax state, or under tension/motion state based upon the interval between the two peaks detected at step S11. Alternatively, this zone length may be determined by entering a value by an operator. For instance, the length of the zone Z may be set to 20% of the time "t" during the rest/relax state, and may be set to 10% of the time "t" during tension/motion state. As previously explained, since the zone "Z" is increased or decreased in response to the conditions of the subject under examination, the pulse waves can be certainly detected by further suppressing the consumption power.

Also, while the length of the zone Z (value of Y) may be made large for a time period close to the commencement of the drive operation, this length of the zone Z may be thereafter made small in response to pulse rates and pulsation intervals. As a result, the error detection of the pulse waves occurring after a short time period from the commencement of measurement can be reduced, and also the zone z may be set in connection with the actual pulse wave conditions of the subject under examination, so that the power consumption can be suppressed.

After these two peaks larger than, or equal to the predetermined threshold, pulse waves produced based upon the reflection wave "f1" are continuously inputted to the pulsation detecting unit 41. Then, the control unit causes the pulsation detecting unit 41 to detect a peak based upon the newly entered pulse waveforms, and then executes the pulsation detecting process in order to determine as to whether or not the peak of the new pulse wave is caused by the pulsation based on both the timing of this peak and the zone set by the zone setting process (step S13) at a step S15.

In the pulsation specifying process, in such a case that there is only one peak detected within the zone "Z", the control unit determines that this single peak corresponds to the pulsation. In the case that there are plural peaks within this zone Z, the control unit may determine that among these plural peaks, such a peak which is detected at a timing located nearest with respect to the timing of the predicted pulsation is caused by the pulsation. When the peak caused by the pulsation is determined, the control unit reads out the occurrence timing of such a peak corresponding to the pulsation from the timing which is recorded in correspondence with the pulse waves, and then stores the read occurrence timing into the storage unit.

It should also be noted that when a plurality of peaks are detected within the zone Z, the control unit may specify that such a peak having a larger value is caused by the pulsation.

Then, when the peak corresponding to the pulsation is specified (YES at step S17), the pulse rate calculating unit 42 calculates a pulse rate "N" based upon both the timing of the peak specified as the pulsation and the timing of a peak of a preceding pulsation which is stored in the storage unit. The display unit 41 digitally displays the supplied pulse rate "N" on the liquid crystal display screen in combination with the pulse waveform. Furthermore, in response to the supplied pulse signal, the display unit 41 indicates the presence of pulses by a flickering green color indication. Thus, the user can visibly recognize their own pulse waves, by observing this green-colored flickering indication.

Alternatively, since pulse sounds are outputted in response to the supplied pulse signal, the user may audibly recognize presence of their own pulsations.

In the pulsation determining process operation (step S15), in such a case that such a peak which is larger than, or equal to the predetermined value is not detected within the zone Z (namely, when the timing of pulsation is not acquired) (NO at step S17), the control unit executes a time out process (step S25).

As this time out process, the following various process operations are involved. That is, a time out process operation is accomplished by changing a setting condition in such a manner that the peak corresponding to the pulsation may be easily detected, such as while the value of the changing ratio "Y" is increased, the zone "Z" is widely set, and the predetermined value used to detect the peak within the zone Z is increased. Another time out process operation is accomplished by drawing attention to a person applied with the sensor in such a manner that beep sounds are produced, and a message that there is a possibility the position of the sensor is shifted is displayed on the display unit 41. Also, another time out process operation is accomplished by assuming that a pulse is detected at the predicted timing of the pulsation, the timing of the peak of the pulsation is stored in the memory, and the pulse rate "N" is calculated to be displayed.

When the pulsation detecting unit 41 detects such a peak specified as the desirable pulsation at step S15 (YES at step S17), and also after the time out process operation is carried out (after step S25), the control unit checks as to whether or not the end instruction is issued (step S31). When such an end instruction is not issued (NO at step S31), the process operation is returned to the previous step S11. At this step S11, the control unit predicts timing of the next pulsation based upon both the latest pulsation and the timing of the two peaks corresponding to one pulsation appeared before the latest pulsation, and then, repeatedly performs the similar process.

In the case that the end instruction is issued (YES at step S23) after the warning process is carried out (after step S21), and also the end instruction is detected (YES at step S31) after the time out process is carried out, the control unit stops the operation of the driver circuit 12 so as to stop the oscillation of the ultrasonic waves from the oscillator 11. Also, the control unit executes an end process, such as interruption of the peak detecting process by the pulsation detecting unit. Then, the control unit accomplishes the pulse wave detecting process operation.

As previously described, in accordance with this first embodiment, the peak which is not involved in the preselected time range (zone Z) may be handled as noise, whereas the pulsation may be determined only from the peak produced within the zone Z. As a result, the storage capacity of the storage unit and the calculation amount may be reduced.

Also, since the frequency analysis is not utilized in this pulse wave detecting apparatus, such noise which is produced in the irregular mode may also be recognized as noise.

Furthermore, since the peaks corresponding to the respective pulsations are detected, the change contained in the pulse rate for every pulsation and the fluctuations of the pulsations can be detected.

Embodiment 2

Next, a pulse wave detecting apparatus according to a second embodiment of the present invention will now be described.

It should be understood that since an arrangement of this pulse wave detecting apparatus of the second embodiment is similar to that of the first embodiment except for functions and operations of the respective units and a portion of output signals, only different functions will be explained and descriptions of the same portions are omitted.

In the second embodiment, while a zone "Z" is subdivided into a plurality of zones, the control unit judges as to whether or not a peak of a detected pulse waveform is equal to a peak corresponding to a pulsation based upon in which zone the timing of this detected pulse wave peak is located. The zone "Z" contains both a "I-th" zone (first zone) located in front of timing of a predicted pulsation, and a "II-th" zone (second zone) containing timing of zone-predicted pulsation. In this second embodiment, the zone "Z" is constituted by only these two zones. With respect to a peak which is detected in the I-th zone, a decision as to whether or not this detected peak corresponds to the pulse is reserved. With respect to a peak which is detected in the II-th zone, the control unit immediately specifies that this detected peak corresponds to the pulsation and accomplishes the determining process of the pulsation, and then commences both a timing prediction of a next pulsation and zone setting. As previously explained, depending upon which zone the timing of the detected peak is included, the control unit executes a different process. When probability at which the peak corresponds to the pulsation is high, the control unit immediately specifies that this peak signal may correspond to the pulsation, and accomplishes the pulsation determining process. As a result, the control unit can specify the desirable pulsation, while using a smaller calculation amount and a smaller storage capacity.

A main flow operation of a pulse wave detecting process according to the second embodiment is similar to that of the above-explained first embodiment shown in FIG. 2. That is, timing of two peaks is firstly acquired, and then the control unit predicts timing of a next pulsation based upon the acquired peak timing (steps S1 to S11 of FIG. 2). Then, after the timing of the pulsation is predicted, the control unit performs a zone setting process operation.

Figure 7:
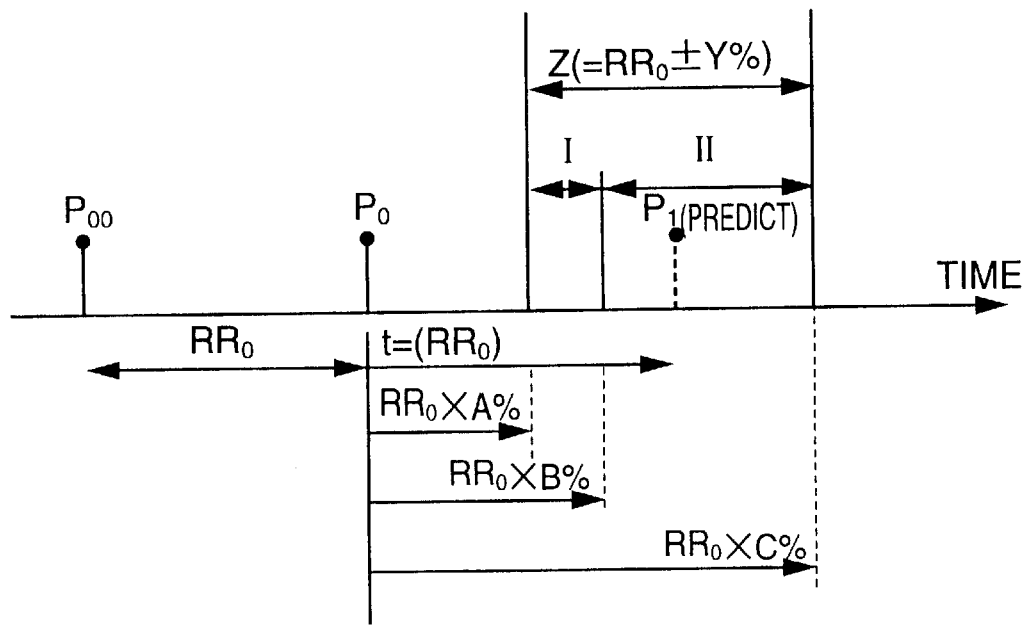
FIG. 7 is an explanatory diagram for explaining predictions of subsequent pulsation timing by a pulsation detecting unit, and also setting operation of zones in a pulse wave detecting apparatus according to a second embodiment of the present invention.

FIG. 7 is an explanatory diagram for explaining predictions of subsequent pulsation timing, and also setting of zones in the pulse wave detecting apparatus of the second embodiment.

As represented in FIG. 7, in the zone setting process according to the second embodiment, the zone Z similar to that of the first embodiment, the I-th zone, and the II-th zone are determined.

The I-th zone is set within a time range earlier than the timing of the predicted pulsation "P1" in the zone Z. The II-th zone is set over such a time range within the zone Z except for the I-th zone, and is set to a time period after the I-th zone, while containing the timing of the predicted pulsation P1.

The range of the zone Z is similar to the range of the first embodiment. This range of the zone Z is set to ±Y% of the timing of the predictable next pulsation. A starting point of this zone Z is equal to such a time instant defined from a peak "P0" of a pulsation immediately before the predictable next pulsation to after t×(100−Y)/100. An end point of this zone Z is equal to such a time instant defined from the peak "P0" to after t×(100+Y)/100.

Then, the I-th zone uses the same time instant as that of the zone Z as a starting point. Both an end point of the I-th zone and a starting point of the II-th zone are set as from the peak "P0" of the pulsation immediately before the predictable next pulsation to t×(100−M)/100. Note that Y>M>0. An end point of the II-th zone corresponds to the same time instant as the end point of zone Z.

It should be noted that the starting points of the zone Z and the I-th zone, both the end point of the I-th zone and the starting point of the II-th zone may be calculated, while ratios of pulsation interval "RR0" from the peak "P0" are previously determined as , B%, and C% respectively. Note that A=100−Y, B=100−M, C=100+Y.

Then, after the zone setting process has been carried out, the pulsation detecting process is executed.

In the pulsation detecting process of the second embodiment, among such peaks of pulse waves, a peak which is produced at timing outside the range of the zone Z is assumed as such a peak which is caused not by a pulsation, but by noise. Also, as to peaks which are produced at a timing within the range of the zone Z, such a peak which is located near the predicted timing is assumed to be caused by the pulsation. The pulsation detecting process operation based upon such a fact as to whether the detected timing corresponds to the I-th zone, or to the II-th zone is carried out.

Figure 8:
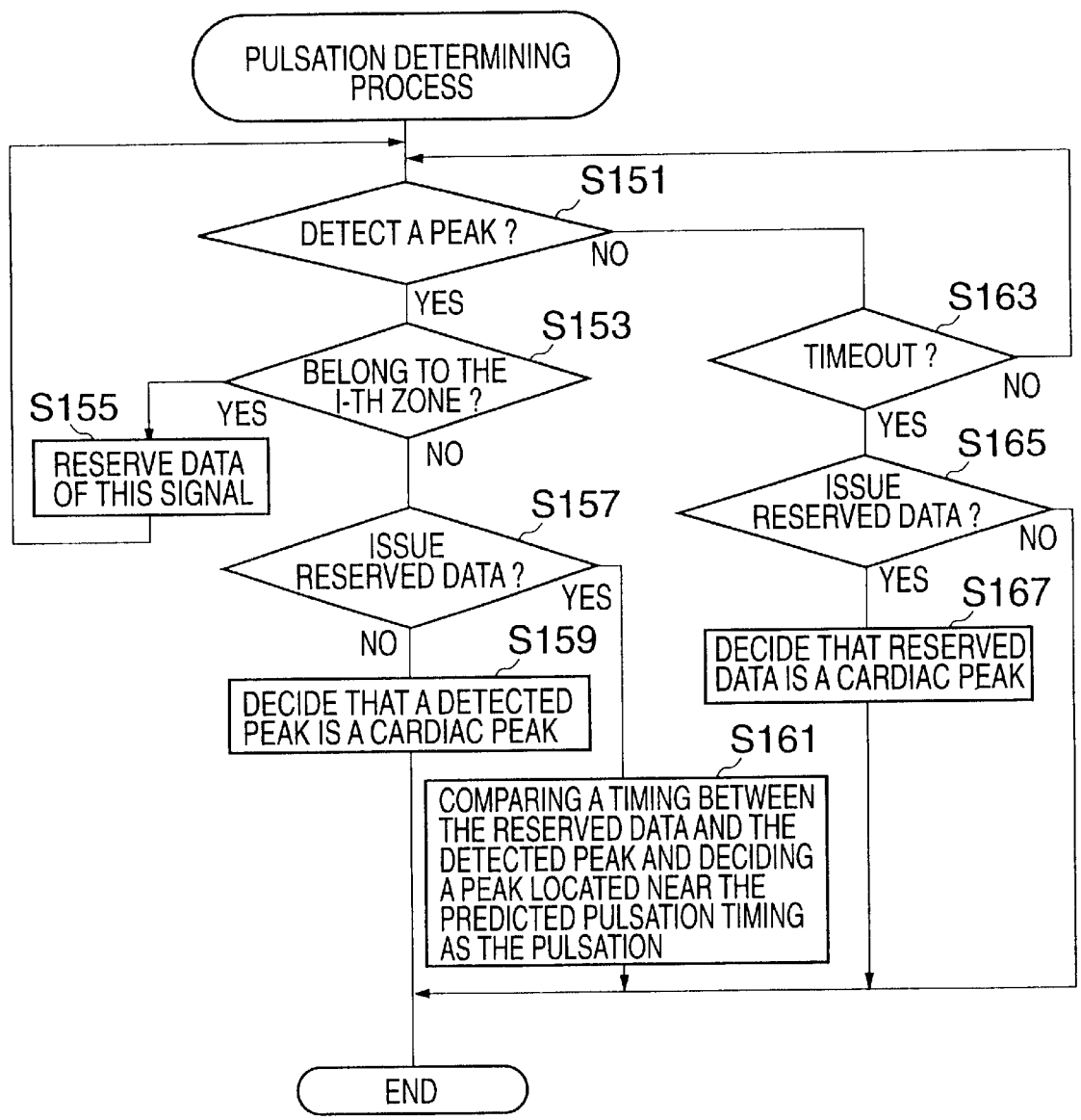
FIG. 8 is a flow chart for explaining a flow operation of a pulsation determining process executed by the pulse wave detecting apparatus of the second embodiment.

FIG. 8 is a flow chart for explaining a flow operation of a pulsation determining process executed by the pulsation detecting unit 41 according to the second embodiment.

When the zone setting process is ended and thereafter the pulsation determining process is commenced, as shown in FIG. 8, the pulsation detecting unit 41 monitors as to whether or not a peak of a pulse waveform is detected (step S151). Then, when such a peak is detected (YES at step S151), the control unit of the pulsation detecting unit 41 checks as to whether or not the timing of the acquired peak belongs to the I-th zone (step S153). When this peak timing is entered into the I-th zone (YES of step S153), the I-th zone is set in front of the predicted timing of the next pulsation. Thus, there is a possibility that another peak which is located at a nearer position with respect to the predicted timing may be detected. Therefore, the control unit reserves a decision as to whether or not this detected peak corresponds to the pulsation or noise, and stores the data of this detecting timing into the memory (step S155). At this time, in the case that the data about the peak has already been stored into the memory, since such a peak which is detected later than the peaks which have been detected within the I-th zone is located near the predicted timing, the control unit deletes the stored data, and then rewrites data about a new peak signal into the storage area of the memory. As a consequence, the data related to a peak which is detected at the latest stage within the I-th zone is continuously stored into the storage area where the data of this detected peak signal has been stored. Then, the process operation is returned to the previous step S151 at which the control unit checks as to whether or not a peak is present.

In the case that the peak is detected (YES at step S151) and the timing of this detected peak is entered in the II-th zone (NO at step S153), the control unit checks as to whether or not the storage unit saves such data (reserved data) of the timing of the peak which has been reserved and stored (step S157). When there is no reserved data, there is a great possibility that this detected peak is located near the predicted timing, as compared with another peak which will be detected later. As a result, the control unit confirms that this detected peak is caused by the cardiac peak, and thus specifies the pulsation (step S159).

In such a case that the reserved data is stored in the memory, this reserved data corresponds to data detected within the I-th zone. The control unit compares a shift between the detected data and the predicted pulsation timing with another shift between the reserved data and the detected data, and then, specifies such a peak located near the predicted pulsation timing as the pulsation (step S161).

On the other hand, when the peak is not detected at step S151 (NO at step 151), the control unit checks as to whether or not the present time instant is located within the zone "Z" (step 163). In the case that the present time instant has elapsed over the zone "Z" and is entered to the time-out zone (YES at step 163), the control unit checks as to whether or not the reserved data is stored in the storage unit (step 165). In the case that the data is stored in the storage unit, this reserved data corresponds to data of such a peak which is detected at the latest timing. Then, the control unit specifies that the peak of this reserved data corresponds to the pulsation.

In the case that no peak is detected and the process operation is not entered into the time-out zone, the process operation is returned to the previous step 151 at which the control unit continues to monitor as to whether or not a peak is detected.

After the peak corresponding to the pulsation is determined (after step S159 and after step S161), and also when the process operation is entered into the time-out zone while the peak is not detected (NO at step 165), this pulsation determining process is accomplished.

Similar to the first embodiment, after the pulsation determining process has been carried out, the process defined after step S17 of FIG. 2 is carried out. In other words, the control unit executes the time out process operation if necessary, depending on whether or not the peak corresponding to the pulsation is determined in the pulsation determining process operation (FIG. 8), and repeatedly performs the processes defined subsequent to the timing prediction of the next pulsation (step S11 of FIG. 2) until the end instruction by such as the operator is entered.

When the end instruction is issued, the pulse wave detecting process is directly accomplished.

As previously described, in accordance with the second embodiment, the zone "Z" of a predetermined range located before/after the predictable pulsation is segmented into the I-th zone located earlier than the predicted timing of the pulsation, and also the II-th zone subsequent to the I-th zone, which includes the predicted pulsation. Among the peaks of the pulse waves detected within the I-th zone, only such data related to the latest peak is stored in the storage unit, so that the necessary storage capacity can be reduced.

Also, in such a case that the pulse wave is not detected within the I-th zone, but is first detected within the II-th zone, since the peak of this detected pulse wave which is caused by the pulsation is specified, both the storage capacity and the calculation amount can be reduced.

In such a case that the peak of the pulse waveform is detected within the I-th zone and the peak of the pulse waveform is detected within the II-th peak under such a state that the data is stored in the storage unit, the control unit immediately compares only such a peak whose data is stored in the storage unit with the peak detected within the II-th zone (namely, the first peak detected within the II-th zone) so as to determine the peak corresponding to the pulsation. As a consequence, the peak corresponding to the pulsation can be determined within a short time period, while requiring a small storage capacity and also a small calculation amount. Also, the comparison of these two peaks is carried out by executing such a simple calculation that the predictable pulsation timing is simply compared with the time interval. As a result, as to this simple comparison operation, the peak corresponding to the pulsation can be determined within such a short time period, while requiring only such a small storage capacity as well as a small calculation amount.

As previously described, in accordance with the second embodiment, since the pulsation may be determined before the entire range of the zone Z has elapsed, the peak corresponding to the pulsation may be detected within a short time duration, while both the calculation amount and the required storage capacity are suppressed to smaller values.

Also, since the frequency analysis is not utilized in this pulse wave detecting apparatus, such noise which is produced in the irregular mode may also be recognized as noise.

Furthermore, since the peaks corresponding to the respective pulsations are detected, the change of the pulse rate for every pulsation and the fluctuations of the pulsations can be detected.

Embodiment 3

Next, a pulse wave detecting apparatus according to a third embodiment of the present invention will be described.

It should be understood that since an arrangement of this pulse wave detecting apparatus of the third embodiment is similar to that of the first embodiment except for functions and operations of the respective units and a portion of output signals, only different functions will be explained and descriptions of the same portions are omitted.

In this third embodiment, while a zone "Z" is subdivided to be set into a plurality of zones, the control unit judges as to whether or not a peak of a detected pulse waveform is equal to such a peak corresponding to a pulsation based upon which zone the timing of this detected pulse wave peak is located. The zone "Z" contains both a "I-th" zone (first zone) located in front of timing of a predicted pulsation, and a "II-th" zone (second zone) containing timing of zone-predicted pulsation. In this third embodiment, the zone "Z" is constituted by three zones made of both the I-th zone and the II-th zone, and a "III-th" zone subsequently to the II-th zone. Then, with respect to a peak which is detected in the I-th zone, a decision as to whether or not this detected peak corresponds to the pulse is reserved. With respect to a peak which is detected in the II-th zone, the control unit immediately specifies that this detected peak corresponds to the pulsation and accomplishes the determining process of the pulsation, and then commences both a timing prediction of a next pulsation and a zone setting operation. As previously explained, depending on which zone the timing of the detected peak is included, the control unit executes the different process operation. When probability at which the peak corresponds to the pulsation is high, the control unit immediately specifies that this peak signal may correspond to the pulsation, and accomplishes the pulsation determining process. As a result, the control unit can specify the desirable pulsation, while using a smaller calculation amount and a smaller storage capacity.

A main flow operation of a pulse wave detecting process operation according to the third embodiment is similar to that of the above-explained first embodiment shown in FIG. 2. That is, timing of two peaks is first acquired, and then the control unit predicts timing of a next pulsation based upon the acquired peak timing (steps S1 to S11 of FIG. 2). Then, after the timing of the next pulsation is predicted, the control unit performs a zone setting process operation.

Figure 9:
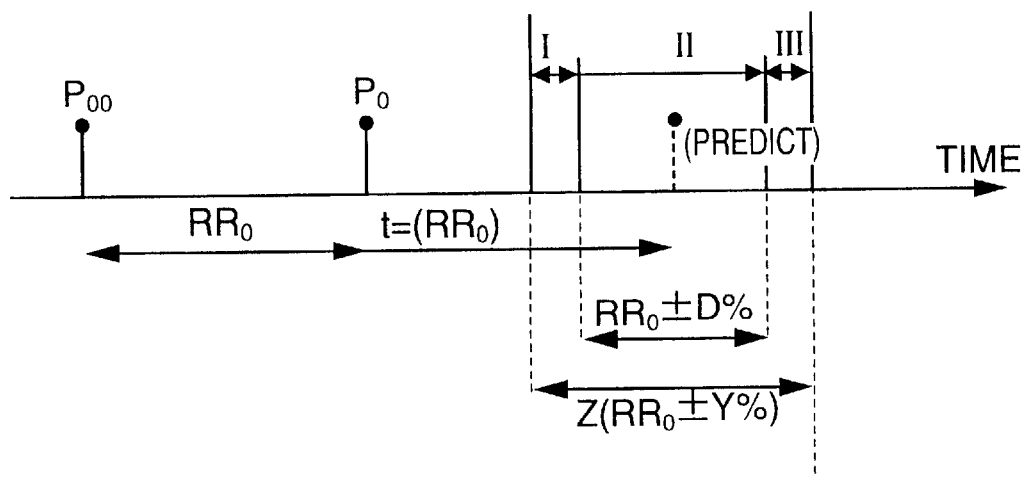
FIG. 9 is an explanatory diagram for explaining predictions of subsequent pulsation timing by a pulsation detecting unit, and also setting operation of zones in a pulse wave detecting apparatus according to a third embodiment of the present invention.

FIG. 9 is an explanatory diagram for explaining predictions of subsequent pulsation timing, and also setting operation of zones executed by the pulsation detecting unit 41 in the pulse wave detecting apparatus of the third embodiment.

As represented in FIG. 9, in the zone setting process according to the third embodiment, the zone Z similar to that of the above-explained embodiment, the I-th zone, the II-th zone, and the III-th zone are determined.

The I-th zone is set within a time range earlier than the timing of the predicted pulsation "P1" in zone Z. The II-th zone corresponds to such a zone within zone Z except for the I-th zone, and is set to a time period after the I-th zone, while containing the timing of the predicted pulsation P1. The III-th zone is set over such a time range subsequent to the II-th zone. In this third embodiment, the II-th zone is set to be equal to D% (Y>D>0) of the pulsation interval RR0 located before/after the predicted timing of the pulsation P1. Also, the time elapse of the I-th zone is made equal to the time elapse of the III-th zone.

The range of the zone Z is similar to the range of the first embodiment. This range of the zone Z is set to ±Y% of the timing of the predictable next pulsation. A starting point of this zone Z is equal to such a time instant defined after t×(100−Y)/100 from a peak "P0" of a pulsation immediately before the predictable next pulsation. An end point of this zone Z is equal to such a time instant defined after t×(100+Y)/100 from the peak "P0".

Then, the I-th zone uses the same time instant of the starting point as that of the zone Z as a starting point. Both an end point of the I-th zone and a starting point of the II-th zone are set as t×(100−D)/100 from the peak "P0" of the pulsation immediately before the predictable next pulsation. Note that Y>M>0.

Both and end point of the II-th zone and a starting point of the III-th zone are set as t×(100+D)/100 from the peak "P0" of the pulsation immediately before the predictable next pulsation. An end point of the III-th zone is equal to the end point of the zone "Z".

It should be noted that the starting points of the zone Z and the I-th zone, both the starting point of the II-th zone and the ending point of the I-th zone, the starting point of the III-th zone and the ending point of the II-th zone, and also the end points of the zone Z and the III-th zone may be calculated, while ratios of pulsation interval "RR0" from the peak "P0" are previously determined as A%, D%, E% and C% respectively. Note that A=100−Y, D=100−D, E=100+D, and C=100+Y.

Then, after the zone setting process operation has been carried out, the pulsation detecting process is executed.

In the pulsation detecting process of this third embodiment, among such peaks of pulse waves, a peak which is produced at a timing outside the range of the zone Z is assumed as a peak which is caused not by a pulsation, but by noise. Also, as to peaks which are produced at timings within the range of the zone Z, such a peak which is located at the nearest position as to the predicted timing is assumed to be caused by the pulsation. The pulsation detecting process operation based upon such a fact as to whether the detecting timing corresponds to any one of the I-th zone through the III-th zone is carried out.

FIG. 10 is a flow chart for explaining a flow operation of a pulsation determining process executed by the pulsation detecting unit 41 according to the third embodiment.

As indicated in FIG. 10, in the pulsation detecting process, the pulsation detecting unit 41 detects a peak from a pulse waveform (step S251). Then, when such a peak is detected (YES at step S251), the control unit of the pulsation detecting unit 41 checks as to whether or not the timing of the acquired peak belongs to the I-th zone (step S253). When this peak timing is entered in the I-th zone (YES of step S253), there is a possibility that another peak which is located nearer with respect to the predicted timing will be detected later. Therefore, the control unit reserves a decision as to whether or not this detected peak corresponds to the pulsation, and stores the data of this detection timing into the memory (step S255).

At this time, in the case that the data about the peak has already been stored into the memory, the data which has already been acquired corresponds to a peak which was previously detected within the I-th zone. Among the peak signals detected in the I-th zone, such a peak signal which is detected later is approximated to the predicted timing. Accordingly, the control unit deletes the stored data, and then rewrites data of a new peak signal into the storage area of the memory.

Then, the process operation is returned to the previous step S251.

In the case that the peak is detected (YES at step S251) and the timing of this detected peak is entered into the II-th zone (NO at step S253 and YES at step S261), the II-th zone is located close to the predicted timing of the pulsation, as compared with other zones, namely the I-th zone and the III-th zone. As a result, the control unit determines that this peak detected in the II-th zone corresponds to the pulsation irrespective of a fact as to whether or not the data saved in the storage unit is present, without waiting for the peak detection result in the III-th zone (step S263). Then, the pulsation determining process operation is accomplished.

In the case that a peak of a pulse waveform is detected within the III-th zone (YES at step S251, NO at step S253, and NO at step S261), if the peak of the pulse waveform is detected in the II-th zone, then the pulsation detecting process operation should be accomplished. Therefore, such a peak of the pulse waveform could not be detected in the II-th zone. Then, the pulsation detecting unit 41 checks as to whether or not the reserved data is stored in the storage unit (step S265). When such reserved data is not stored in the storage unit (NO at step S265), the peak is first detected in the III-th zone. Since the III-th zone corresponds to such a time range after the predicted timing of the pulsation, the peak detected in this III-th zone is located close to the predicted timing of the pulsation, as compared with a peak which is detected later. As a consequence, the pulsation detecting unit 41 determines that this peak corresponds to the pulsation (step S269), and then the pulsation determining process is ended.

In the case that a peak signal is detected in the III-th zone and also there is such data which has already been stored in the storage unit (YES at step S265), this previously-stored data corresponds to such timing which is located close to the latest pulsation, namely the predicted pulsation among the peaks detected within the I-th zone. Then, the control unit compares a shift between one timing of a newly detected peak within the III-th zone and the predicted timing of the pulsation with another shift between another timing of a newly detected peak within the III-th zone and the predicted timing of the pulsation. Then, the control unit determines that such a peak located close to the predicted timing of the pulsation may correspond to the pulsation (step S267), and accomplishes the pulsation determining process operation. As a consequence, a peak located at the nearest position with respect to the predicted timing of the pulsation among the peaks detected within the I-th zone, and the peak detected in the III-th zone, the control unit specifies the peak located closer to the predicted timing of the pulsation as the peak caused by the pulsation.

In such a case that while no peak is detected at step S251. (NO at step S251), the zone "Z" has elapsed and the process operation is brought into the time-out state (YES at step S257), the control unit checks as to whether or not there is a saved data. At this time, the saved data is equal to data about the latest peak among the peaks which are detected in the I-th zone. Then, when there is a saved data (YES at step S258), the control unit determines that this peak corresponds to the pulsation, and stores this data into a predetermined memory area of the storage unit (step S259). Then, the pulsation determining process operation ends.

In a case that the peak is not detected (NO at step S251), the process operation is brought into the time-out state (YES at step S257), and the saved data is not present (NO at step S258), this process operation is brought into the time-out state while no peak is detected since the commencement of the pulsation determining process operation. At this time, the control unit executes an end process operation while the pulsation is not specified, and then accomplishes the pulsation determining process.

Similar to the first embodiment, after the pulsation determining process operation has been carried out, the process operation defined after step S17 of FIG. 2 is carried out. In other words, the control unit executes the time out process, if necessary, depending whether or not the peak corresponding to the pulsation may be determined in the pulsation determining process (FIG. 10), and repeatedly performs the process operations subsequent to the timing prediction of the next pulsation (step S11 of FIG. 2) until the end instruction is entered by the operator or the like.

When the end instruction is issued, the pulse wave detecting process operation is directly accomplished.

As previously described, in accordance with the third embodiment, the zone "Z" of a predetermined range located before/after the predictable pulsation timing is segmented into the I-th zone located earlier than the predicted timing of the pulsation, and the II-th zone subsequent to the I-th zone which includes the predicted pulsation, and also the III-th zone subsequent to the II-th zone. Among the peaks of the pulse waves detected within the I-th zone, only such data related to the latest peak is stored in the storage unit, so that the necessary storage capacity can be reduced.

Also, in such a case that the pulse wave is not detected within the I-th zone, but is first detected within the II-th zone, since the peak of this detected pulse wave which is caused by the pulsation is specified, both the storage capacity and the calculation amount can be reduced.

In a case that the peak of the pulse waveform is detected within the I-th zone and the peak of the pulse waveform is detected within the III-th peak under such a state that the data is stored in the storage unit, the control unit immediately compares only such a peak whose data is stored in the storage unit with the peak detected within the III-th zone (namely, first peak detected within III-th zone) so as to determine the peak corresponding to the pulsation. As a consequence, the peak corresponding to the pulsation can be determined within a short time period, while requiring a small storage capacity and also a small calculation amount. Also, this comparison operation of these two peak is carried out by executing such a simple calculation that the predictable pulsation timing is simply compared with the time interval. As a result, as to this simple comparison operation, the peak corresponding to the pulsation can be determined within such a short time period, while requiring only a small storage capacity and a small calculation amount.

As previously described, in accordance with the third embodiment, since the pulsation may be determined before the entire range of the zone Z elapses, the peak corresponding to the pulsation may be detected within a short time duration, while both the calculation amount and the required storage capacity are suppressed to smaller values.

Also, since the frequency analysis is not utilized in this pulse wave detecting apparatus, such noise which is produced in the irregular mode may also be recognized as the noise.

Furthermore, since the peaks corresponding to the respective pulsations are detected, the change contained in the pulse rate for every pulsation and also the fluctuations of the pulsations can be detected.

Modifications

The various preferred embodiments of the present invention have been described above, but the present invention is not limited thereto, and may be modified, changed, and substituted by other embodiments without departing from the technical scope and spirit of the accompanying scope of claims.

For instance, in the respective embodiments, just after the pulse wave detecting process operation is commenced, two peaks which are larger than, or equal to the predetermined threshold are detected from the pulse waves, and the control unit predicts the subsequent pulsation, while specifying these peaks as the peaks caused by the pulsations (steps S5 to S1). Alternatively, while larger numbers of peaks which are larger than, or equal to a predetermined value are acquired from the pulse waves, an averaged peak interval may be calculated from both the time period of these peak acquisition and the total peak number. Then, the control unit may predict a next pulsation from this averaged peak interval. Alternatively, assuming now that an interval of pulsations just after the pulse wave detecting process operation is commenced is selected to be a predetermined time interval, i.e., 1,000 msec (60 beats/second) and 857 msec (70 beats/second) during the rest state, the control unit may predict a subsequent pulsation based upon this interval. Also, while a plurality of values of intervals obtained during the rest state and of intervals obtained during the tension/motion states are stored in the storage unit, the control unit may predict a next pulsation based upon such an interval selected by the operator.

Also, while a change contained in an interval among a plurality of continuous pulsations within a preselected time interval is acquired and also a change contained in pulsatory beat numbers of continuous pulsations is acquired, the control unit may determine predetermined time "t" from any one of these changes so as to predict a next pulsation. For instance, as indicated in FIG. 11, in such a case that a continuous pulsation interval and also a pulse rate are reduced by approximately 7%, assuming now that a next pulsation interval is also equal to a range between RR(min) and RR(max) before/after such a value further reduced by 7% from the preceding value, the control unit may predict a next pulsation interval RR0 (=predetermined time "t") based upon this pulsation interval. As previously explained, since the next pulse is predicted by considering the changes contained in the pulsation intervals and the pulse rates, even in a case that the pulse intervals are varied due to such as commencement and end of motion, and tension, the control unit may predict the next pulse with high precision, and therefore may specify that the proper peak is caused by the pulsation from the pulse waveforms.

In the above-explained respective embodiments, the control unit predicts the timing of the next pulsation from the timing of the peak (timing of pulsation) corresponding to the previously acquired pulsation except from such an operation just after the pulse wave detecting process is commenced. The previously acquired timing of the pulsation is employed so as to specify the peak caused by the next pulsation. In addition thereto, for instance, the ultrasonic waves may be transmitted only during a predetermined time interval before/after the predictable pulsation, namely, the previously acquired timing of the pulsation may be commonly used for other operations.

In the above-described various embodiments, while the ultrasonic waves are transmitted, the pulse waves are detected by utilizing a fact that the frequencies of the reflection waves are varied by the pulse waves. The present invention is not limited to this method of detecting the pulse waves, but may, for example, detect the pulse waves while the ultrasonic waves are transmitted, and the amplitudes of the reflection waves are varied by the pulse waves. Alternatively, while a piezoelectric-effect type element is employed as a sensor, a pulse wave may be detected from a pressure change of a skin surface (displacement of skin surface caused by pressure), which is caused by a pressure change occurred inside an artery.

While the pulse wave detecting apparatus of the present invention is assembled in a watch, and also utilizes an oscillator having an oscillation frequency of 32 KHz used in the watch, this assembled pulse wave detecting apparatus may transmit ultrasonic waves to a radial artery and ulnar artery.

In the above-described respective embodiments, while the pulse waves are detected the ultrasonic waves are continuously outputted, and furthermore, the pulse waveforms are detected in the continuous mode. Alternatively, after more than two peaks of the pulse wave forms have been detected and the timing of the next pulsation has been predicted, the ultrasonic waves may be transmitted only for a time period within the range of the zone "Z". Alternatively, pulse waveforms and peaks may be acquired only for a time period within the range of the zone Z.

In accordance with the pulse wave detecting apparatus of the present invention, the next pulse is predicted, and the next pulsation is detected from the pulse wave information within the preselected time periods before/after the predicted pulse, which contains the predictable next pulse. As a consequence, the storage capacity of the pulse wave information and also the calculation amount required to detect the next pulsation can be made small. Moreover, the pulsation can be detected within a short time, and the various information as to the respective pulsations can be acquired.

What is claimed is:

1. A pulse wave detecting apparatus comprising:

pulse wave detecting means for detecting a pulse wave;

pulsation predicting means for predicting timing of a pulsation based upon the pulse wave detected by said pulse wave detecting means;

range determining means for determining predetermined widths located before/after the timing of said pulsation predicted by said pulsation predicting means;

pulsation subject extracting means for extracting a subject for pulsation from the pulse wave detected by said pulse wave detecting means in said predetermined widths determined by said range determining means; and pulsation specifying means for specifying a pulse from among said subjects extracted by said pulsation subject extracting means.

2. A pulse wave detecting apparatus as claimed in claim 1 wherein:

said pulsation predicting means predicts the timing of the next pulsation based upon an interval of previously acquired pulsations, or a pulse rate.

3. A pulse wave detecting apparatus as claimed in claim 1 wherein:

said pulsation specifying means determines a pulse based upon both the timing predicted by said pulsation predicting means and the timing of said pulsation subject extracted by said pulsation subject extracting means.

4. A pulse wave detecting apparatus as claimed in claim 2 wherein:

said pulsation specifying means determines a pulse based upon both the timing predicted by said pulsation predicting means and the timing of said pulsation subject extracted by said pulsation subject extracting means.

5. A pulse wave detecting apparatus as claimed in claim 3 wherein:

said range determining means subdivides the predetermined widths located before/after the predicted timing of the pulsation into a plurality of zones containing both a first zone located earlier than the predicted timing of the pulsation and a second zone subsequent to said first zone which contains the predicted timing of the pulsation, and determines the predetermined widths; and said pulsation specifying means immediately specifies a pulsation subject which is first detected in said second zone as the pulsation.

6. A pulse wave detecting apparatus as claimed in claim 4 wherein:

said range determining means subdivides the predetermined widths located before/after the predicted timing of the pulsation into a plurality of zones containing both a first zone located earlier than the predicted timing of the pulsation and a second zone subsequent to said first zone which contains the predicted timing of the pulsation, and determines the predetermined widths; and said pulsation specifying means immediately specifies a pulsation subject which is first detected in said second zone as the pulsation.

7. A pulse wave detecting apparatus comprising:

a pulse wave detector to detect a pulse wave;

a pulsation predicting circuit to predict timing of a pulsation based upon the pulse wave detected by the pulse wave detector;

a range determining circuit to determine predetermined widths located before/after the timing of the pulsation predicted by the pulsation predicting circuit;

a pulsation subject extracting circuit to extract a subject for pulsation from the pulse wave detected by the pulse wave detector in said predetermined widths determined by the range determining circuit; and a pulsation specifying circuit to specify a pulse from among the subjects extracted by the pulsation subject extracting circuit.

* * * * *